(12) United States Patent
Guala

(10) Patent No.: US 7,247,153 B2
(45) Date of Patent: Jul. 24, 2007

(54) CANNULA WITH PROTECTION CAP FOR MEDICAL INFUSION LINES AND THE LIKE

(75) Inventor: Gianni Guala, Turin (IT)

(73) Assignee: Industrie Borla S.p.A., Moncalieri (Turin) (IT)

(*) Notice: Subject to any disclaimer, the term of this patent is extended or adjusted under 35 U.S.C. 154(b) by 303 days.

(21) Appl. No.: 10/626,633

(22) Filed: Jul. 25, 2003

(65) Prior Publication Data

US 2004/0153038 A1 Aug. 5, 2004

(30) Foreign Application Priority Data

Jul. 26, 2002 (IT) .......................... TO2002A0668

(51) Int. Cl.
*A61M 5/32* (2006.01)
*A61M 19/00* (2006.01)
*A61M 5/31* (2006.01)

(52) U.S. Cl. ...................... 604/414; 604/411; 604/192; 604/243

(58) Field of Classification Search ................ 604/411, 604/414, 6.05, 43, 44, 181, 187, 188, 262, 604/272–274, 264, 533, 110, 192, 263, 240, 604/905, 243

See application file for complete search history.

(56) References Cited

U.S. PATENT DOCUMENTS

| 4,740,205 | A | * | 4/1988 | Seltzer et al. ............... 604/192 |
| 4,883,470 | A | * | 11/1989 | Haindl ....................... 604/192 |
| 5,135,489 | A | | 8/1992 | Gordon et al. |
| 5,360,404 | A | | 11/1994 | McLean et al. |
| 6,183,464 | B1 | * | 2/2001 | Sharp et al. ................. 604/533 |
| 6,565,541 | B2 | * | 5/2003 | Sharp ......................... 604/192 |

FOREIGN PATENT DOCUMENTS

DE 201 09 061 U 8/2001

\* cited by examiner

*Primary Examiner*—Tatyana Zalukaeva
*Assistant Examiner*—Leslie Deak
(74) *Attorney, Agent, or Firm*—Sughrue Mion, PLLC

(57) ABSTRACT

Cannula with protection cap for medical infusion lines and the like, comprising a hollow body provided at one end with a female luer lock connector and at the other end with an axial tubular ferrule. The hollow body and the protection cap are provided with respective formations for mutual torsional coupling acting in the direction of rotation corresponding to the unscrewing of the female luer lock connector relative to a male luer lock connector of the medical line.

4 Claims, 3 Drawing Sheets

CANNULA WITH PROTECTION CAP FOR MEDICAL INFUSION LINES AND THE LIKE

FIELD OF THE INVENTION

The present invention relates to cannulas for medical infusion lines and the like, of the kind comprising a hollow body defining at a first end a female luer lock connector and bearing at a second end an axial tubular ferrule.

In such cannulas, the female luer lock connector is destined to be coupled with a complementary male luer lock connector of a feeding line of an infusion liquid or with a syringe, and the tubular ferrule is adapted to be inserted in an appropriate connector with elastic shutter for the protection of the infusion line.

STATE OF THE PRIOR ART

Traditionally, these cannulas are fitted with a protection cap applied in removable fashion on the hollow body in such a way as to enclose the ferrule until the time of its introduction in the connector. After use, the protection cap is again applied on the tubular ferrule and the female luer lock connector is disengaged from the male luer lock connector to allow the removal of the cannula, which is normally single-use.

The disengagement operation between the female luer lock connector of the hollow body of the cannula and the male luer lock connector of the infusion line may be found difficult, and in any case awkward, because the coupling friction between the respective conical surfaces due to the high friction coefficient of the material (normally polycarbonate) whereof these components are made.

SUMMARY OF THE INVENTION

The object of the present invention is to provide a simple and effective solution to the aforesaid problem.

According to the invention, this aim is reached essentially thanks to the fact that said hollow body and said protection cap are provided with respective mutual torsional coupling formations acting in the direction of rotation corresponding to the unscrewing of said female luer lock connector relative to a male luer lock connector.

Thanks to this solution idea, the separation of the cannula from the male luer lock connector of the medical line can be achieved in a practical, convenient and easy manner using the cap as a control organ to impart a high unscrewing torque to the female luer lock connector of the cannula.

The invention provides for two alternative embodiments, in which the aforesaid torsional coupling formations between the protection cap and the hollow body of the cannula are constituted by complementary, respectively lateral and frontal teeth sets. Said teeth sets are opportunely arranged in such a way as torsionally to couple the protection cap and the hollow body only in the direction of unscrewing of the female luer lock connector, but not in the opposite direction.

BRIEF DESCRIPTION OF THE DRAWINGS

The invention shall now be described in detail with reference to the accompanying drawings, provided purely by way of non limiting example, in which.

DETAILED DESCRIPTION OF THE INVENTION

Figure 1:
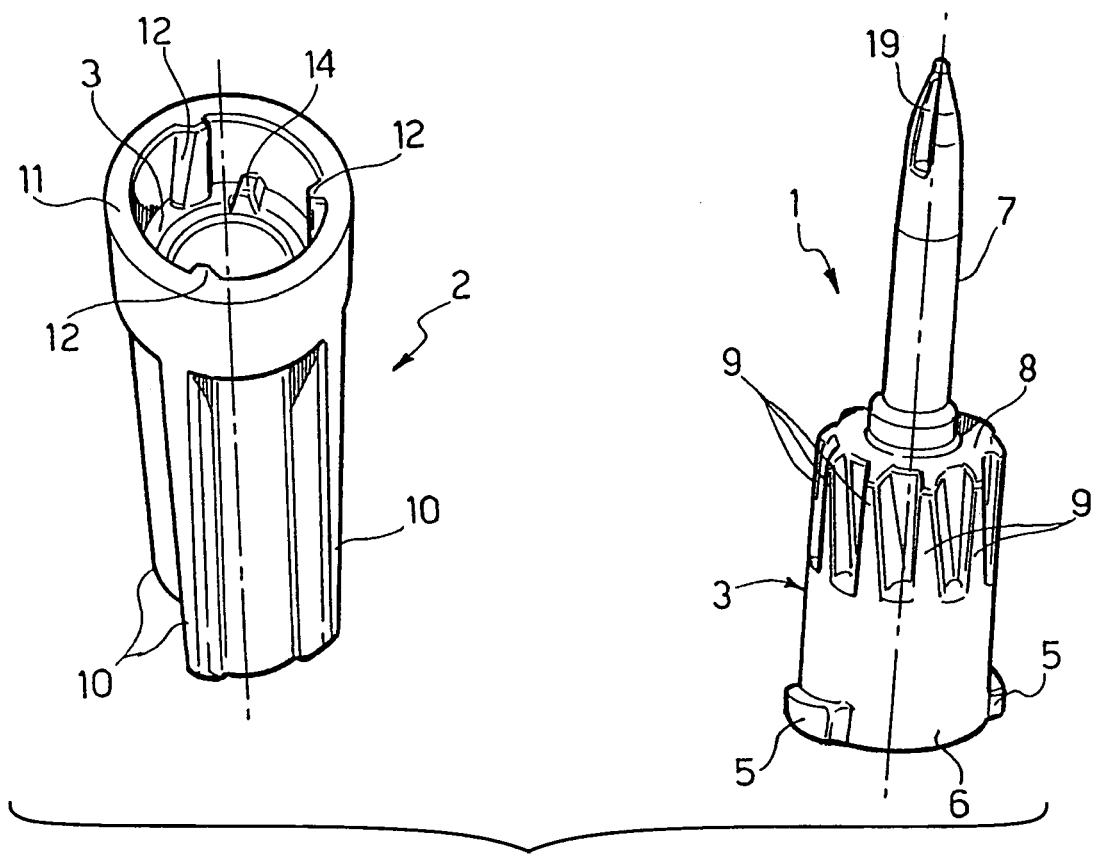
FIG. 1 is an exploded perspective view of a cannula with protection cap according to a first embodiment of the invention.
Figure 2:
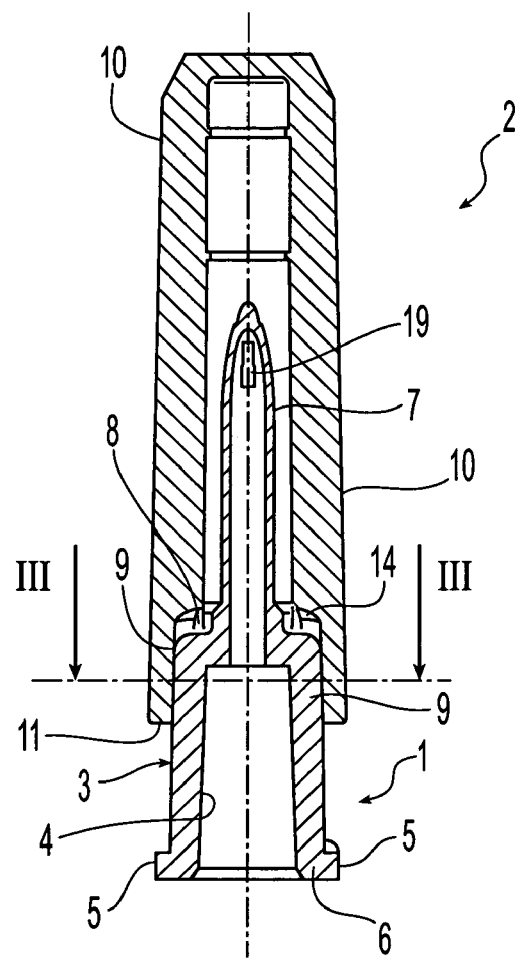
FIG. 2 is an axial section view of the cannula with protection cap according to FIG. 1.
Figure 3:
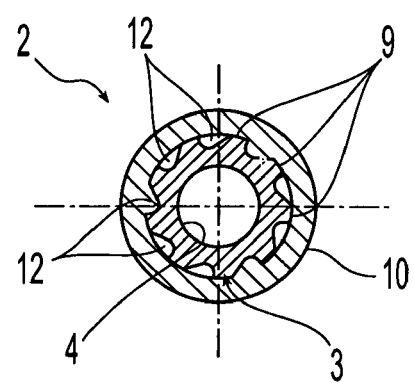
FIG. 3 is a cross section view according to the line III-III of FIG. 2.

Referring initially to FIGS. 1 through 3, the number 1 designates a cannula according to the invention for infusion medical lines and the like, fitted with a protection cap 2.

The cannula 1, normally formed by a single piece of moulded plastic material (conveniently polycarbonate), comprises a hollow body 3 whose cavity, visible in FIG. 2, constitutes a luer cone 4 which in combination with a pair of diametrically opposite external helical teeth 5 formed at an end 6 of the hollow body 3, defines a female luer lock connector, and a tubular ferrule 7 projecting from the other end 8 of the hollow body 3, coaxially thereto. The free end of the ferrule 7 conventionally has a tapered profile with lateral outflow openings 19.

The outer lateral wall of the body 3 is formed for a substantial portion starting from the end 8, with a circumferential annulus of inclined lateral teeth 9 with substantially saw tooth profile, whose function shall be clarified below.

The cap 2, also constituted by a single piece of moulded plastic material, externally has axially elongated projections 10 defining manual grip elements, and it is formed on its inner lateral wall, starting from the edge of its open end 11, with a series of inclined radial teeth 12 with saw tooth profile that is complementary to that of the teeth 9 of the hollow body 3. The teeth 12 extend axially to a an inner annular flange 13 of the cap 2, wherefrom projects an axial stop projection 14.

In the engaged condition of the protection cap 2 on the cannula 1 shown in FIGS. 2 and 3, the open end 11 is engaged by interference on the lateral wall of the hollow body 3 in such a way that the teeth 9 and 12 are mutually coupled in the manner clearly shown in FIG. 3. The stop projection 14 serves as an axial spacer in such a way as to maintain the annular flange 13 of the protection cap 2 distanced from the end 8 of the cannula 3.

The saw tooth shape of the teeth 9 and 12 is such that, when the cap 2 is rotated in a direction relative to the cannula 1, the cap disengages axially relative to the cannula when a predetermined value of torque is reached. This direction of rotation corresponds to the screwing of the luer lock connector 4-5 of the cannula 1 relative to a male luer lock connector of a medical infusion line or the like whereto the cannula 1 is connected in use: with the described arrangement, the torsional uncoupling between the cap 2 and the cannula 1 prevents the luer lock connector 4-5 of cannula 1 from being screwed onto the male luer lock connector of the medical line with excessive torque, which would make difficult their subsequent unscrewing after use. This uncoupling also clearly allows to remove the cap 2 from the cannula 1.

In the reverse direction of rotation, the shape of the teeth 9 and 12 makes the cap 2 positively coupled torsionally with the hollow body 3 of the cannula 1. This direction of rotation corresponds to the unscrewing the luer lock connector 4-5 of the cannula 1 relative to a male luer lock connector of a medical infusion line or the like whereto the cannula 1 is connected in use. This allows to make extremely simple and easy the operations of removing the cannula 1 from said medial line after use, thanks to the rotation manoeuvre operated by rotating the cap 2 by means of the grip parts 10 in such a way as to command the angular displacement of the cap and, by means of the teeth 12 and 9, the simultaneous angular driving of the body 3 in the direction corresponding with the unscrewing of the female luer lock connector 4-5 relative to the male luer lock connector.

Figure 4:
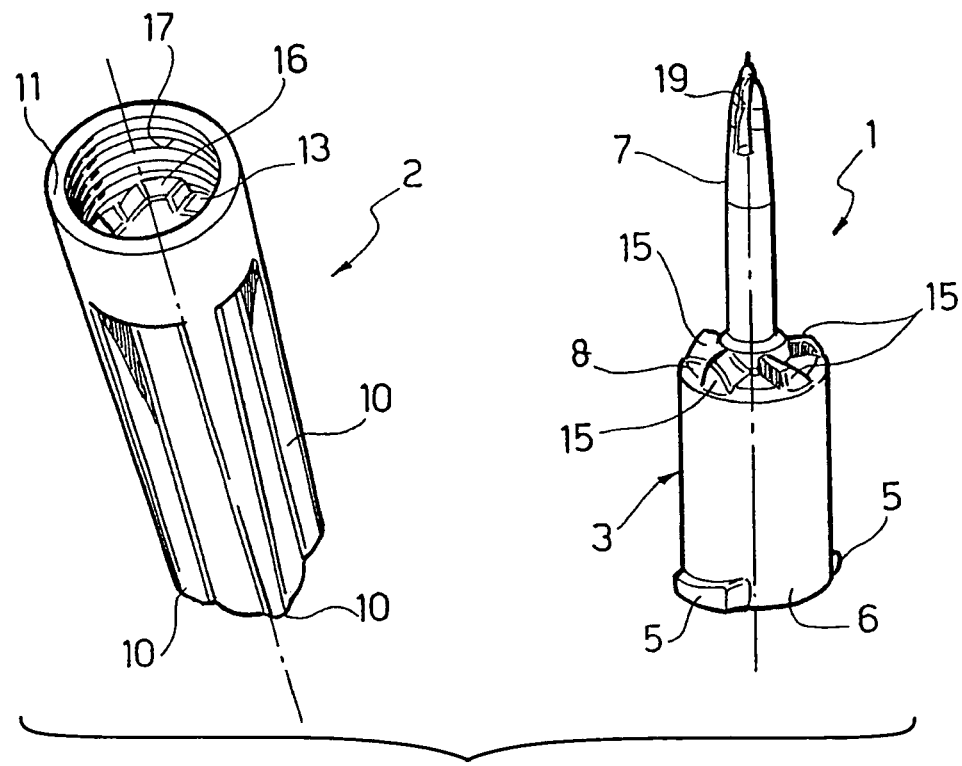
FIG. 4 shows a variation of FIG. 1.
Figure 5:
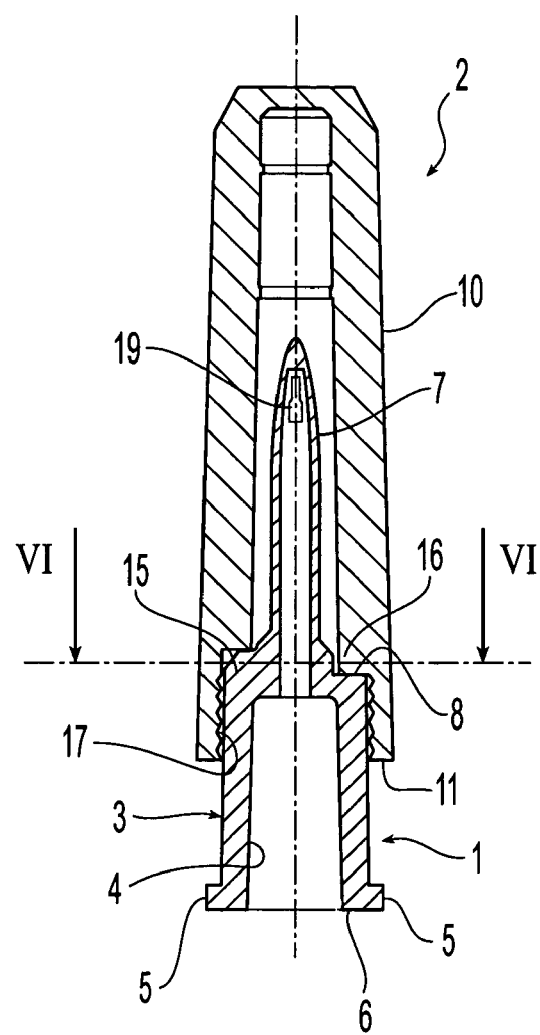
FIG. 5 is an axial section view of the variation of FIG. 4.
Figure 6:
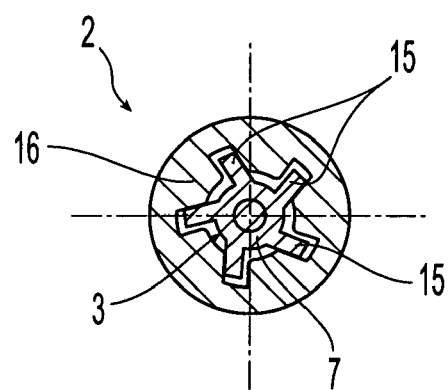
FIG. 6 is a cross section view according to the line VI-VI of FIG. 5.

The variation shown in FIGS. 4 through 6 is generally similar to the embodiment described above, and only the differences will be described in detail below, using the same numeric references for identical or similar parts.

This variation differs from the embodiments of FIGS. 1 through 3 solely in that the lateral teeth 9-12 respectively of the hollow body 3 of the cannula 1 and of the protection cap 2 are replaced by front teeth, designated respectively as 15 and 16.

The front teeth 15 are formed in correspondence with the end 8 of the hollow body 3 around the base of the tubular ferrule 7, whilst the front teeth 16 are obtained in correspondence with the inner annular flange 13 of the cap 2. The inner lateral wall thereof also has, between the annular flange 13 and its open end 11, a helical channel 17.

The operation of this variation is wholly similar to the one described above with reference to the embodiment of FIGS. 1 through 3. In the coupling condition between the cap 2 and the cannula 1, shown in FIGS. 5 and 6, the teeth 15 and 16 are mutually engaged in such a way as to allow and in fact to facilitate the disengagement of the cap 2 making it rotate in one direction, and to make said engagement 2 torsionally integral with the hollow body 3 in the opposite direction of rotation, corresponding to the unscrewing of the female luer lock connector 5-6 from the male luer lock connector of the medical infusion line or the like whereto the cannula is connected in use.

Naturally, the construction details and the embodiments may vary widely from what is described and illustrated herein, without thereby departing from the scope of the present invention as defined in the claims that follow.

What is claimed is:

1. A cannula (1) having a protection cap (2) for a medical infusion line, said cannula comprising a hollow body (3) defining at a first end (6) a female luer lock connector (4-5) adapted to be mated with a male luer lock connector and bearing at a second end an axial tubular ferrule (7), said hollow body (3) having an outer surface formed with lateral teeth (9), and said protection cap (2) having an inner surface formed with complementary lateral teeth (12), wherein said protection cap (2) is configured to be removably applied onto said hollow body (3) to enclose said tubular ferrule (7) with said lateral teeth (9, 12) of said hollow body (3) and said cap (2) is configured to be mutually coupled torsionally for a first direction of rotation corresponding to unscrewing said female leur lock connector (4-5) from said male leur lock connector, and wherein said outer surface of said hollow body (3) and said inner surface of said protection cap (2) are both cylindrical and said lateral teeth (9, 12) of said hollow body (3) and cap (2) have respective included sides configured to torsionally couple said protection cap (2) and said hollow body (3) in a second direction of rotation opposite to said first direction until a predetermined torque is reached and providing axial disengagement of said cap (2) relative to said cannula (1) when said predetermined torque is reached.

2. A cannula as claimed in claim 1, wherein said lateral teeth (9, 12) of said hollow body (3) and cap (2) are axially tapered.

3. A cannula according to claim 1, wherein said lateral teeth (12) of the protection cap (2) terminate within said cap (2) at an inner annular flange (13) having an axial stop projection (14) to space said annular flange (13) from said second end (8) of said hollow body (3).

4. A cannula according to claim 1, wherein said cap (2) comprises external manual actuation parts.

* * * * *